United States Patent [19]
Engelson

[11] Patent Number: 5,944,733
[45] Date of Patent: *Aug. 31, 1999

[54] CONTROLLED DETACHABLE VASOOCCLUSIVE MEMBER USING MECHANICAL JUNCTION AND FRICTION-ENHANCING MEMBER

[75] Inventor: Erik T. Engelson, Menlo Park, Calif.

[73] Assignee: Target Therapeutics, Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/891,936

[22] Filed: Jul. 14, 1997

[51] Int. Cl.[6] .................................................. A61B 17/12
[52] U.S. Cl. ....................................................... 606/191
[58] Field of Search ................... 606/108, 198, 606/158, 157, 153, 152, 194; 128/898; 623/1, 12, 48, 52, 53, 264, 171; 219/225

[56] References Cited

U.S. PATENT DOCUMENTS

| | | | |
|---|---|---|---|
| 3,814,113 | 6/1974 | Morane et al. | 132/36 |
| 4,365,140 | 12/1982 | Bast et al. | 219/225 |
| 4,735,201 | 4/1988 | O'Reilly | 128/303.1 |
| 4,739,768 | 4/1988 | Engelson | 128/658 |
| 4,813,934 | 3/1989 | Engelson et al. | 604/99 |
| 4,884,579 | 12/1989 | Engelson | 128/772 |
| 4,994,069 | 2/1991 | Ritchart et al. | 606/191 |
| 5,108,407 | 4/1992 | Geremia et al. | |
| 5,122,136 | 6/1992 | Guglielmi et al. | 606/32 |
| 5,234,437 | 8/1993 | Sepetka | 606/108 |
| 5,250,071 | 10/1993 | Palermo | 606/198 |
| 5,261,916 | 11/1993 | Engelson | 606/108 |
| 5,292,321 | 3/1994 | Lee | 606/28 |
| 5,304,134 | 4/1994 | Kraus et al. | 604/96 |
| 5,304,195 | 4/1994 | Twyford, Jr. et al. | 606/191 |
| 5,350,397 | 9/1994 | Palermo et al. | 606/200 |
| 5,423,829 | 6/1995 | Pham et al. | 606/108 |
| 5,507,766 | 4/1996 | Kugo et al. | 606/194 |
| 5,522,836 | 6/1996 | Palermo | 606/200 |
| 5,578,074 | 11/1996 | Mirigian | 623/1 |
| 5,676,685 | 10/1997 | Razavi | 606/194 |
| 5,685,322 | 11/1997 | Sung et al. | 128/897 |

FOREIGN PATENT DOCUMENTS

| | | |
|---|---|---|
| 44 45 715 A1 | 6/1996 | Germany . |
| 196 10 333 A1 | 9/1997 | Germany . |
| 7-265431 | 10/1995 | Japan . |
| WO 94/05342 | 3/1994 | WIPO . |

Primary Examiner—Michael Buiz
Assistant Examiner—Vikki Trinh
Attorney, Agent, or Firm—Morrison & Foerster LLP

[57] ABSTRACT

A vasoocclusive member, such as embolic coil, that mechanically joins an instrument for delivering that vasoocclusive member to a selected site within the vasculature or other lumen of a human body via the use of a catheter is provided. A thermoplastic member augments the junction to enhance variously the friction at an integrity of the junction. Once the vasoocclusive member is delivered to the desired site, radio frequency energy is supplied to the thermoplastic member in an amount sufficient to soften the thermoplastic member, allowing mechanical disengagement to then take place.

21 Claims, 4 Drawing Sheets

CONTROLLED DETACHABLE VASOOCCLUSIVE MEMBER USING MECHANICAL JUNCTION AND FRICTION-ENHANCING MEMBER

FIELD OF THE INVENTION

This invention is a surgical instrument and specifically is a device for delivering vasoocclusive members to a selected site within the vasculature or other lumen of the human body via use of a catheter. In particular, the device is an assembly of a vasoocclusive member that mechanically joins an instrument for delivering that vasoocclusive member to the selected site. A thermoplastic member augments this mechanical junction to enhance variously the friction at and integrity of the junction. Once the vasoocclusive member is delivered to the desired site, radio frequency energy is supplied to the thermoplastic member in an amount sufficient to soften the thermoplastic member, allowing mechanical disengagement to then take place.

BACKGROUND OF THE INVENTION

The endovascular treatment of a variety of vascular maladies throughout the body is an increasingly important form of therapy. Catheters have been used to place various treatment materials, devices, and drugs within arteries and veins in the human body. Examples of these vasoocclusive devices and their use in such treatments are shown in U.S. Pat. Nos. 5,234,437 to Palermo and Gia ("Detachable Pusher-Vasoocclusive Coil Assembly with Threaded Coupling") and 5,261,916 to Engelson ("Detachable Pusher-Vasoocclusive Coil Assembly with Interlocking Ball and Keyway Coupling"). These patents show methods and devices for delivery of vasoocclusive members, such as coils, or wires within the human body to sites such as aneurysms, to occlude those sites. Vasoocclusive members such as are discussed in U.S. Pat. No. 4,994,069 to Ritchart et al. may be of a regular or helical configuration or assume a random convoluted configuration at the selected site. The vasoocclusive members normally are made of a radiopaque, biocompatible metal such as platinum, gold, tungsten, or alloys of these and other metals.

In treating aneurysms, it is common to place one or more vasoocclusive members within the aneurysm. The vasoocclusive members occlude the site by posing a physical barrier to blood flow and by promoting thrombus formation at the site.

Vasoocclusive members have typically been placed at the desired site within the vasculature using a catheter and a pusher. The site is first accessed by the distal end of a catheter. In treating peripheral or neural conditions requiring occlusion, the sites are accessed with flexible, small diameter catheters such as those shown in U.S. Pat. Nos. 4,739,768 to Engelson and 4,813,934 to Engelson and Daniels. The catheter may be guided to the site through the use of guidewires (see U.S. Pat. No. 4,884,579 to Engelson) or by flow-directed means such as balloons placed at the distal end of the catheter. Use of guidewires involves the placement of relatively long, torqueable proximal wire sections within the catheter, which proximal sections are attached to more flexible distal end wire section designed to be advanced across sharp bends at vessel junctions. The guidewire is visible using x-ray and allows a catheter to be manipulated through extremely tortuous vessels, even when such vessels are surrounded by soft tissue such as the brain.

Once the selected site has been reached, the catheter lumen is cleared by removing the guidewire (if a guidewire has been used), and the vasoocclusive member is placed into the proximal open end of the catheter and advanced through the catheter with a pusher. Pushers are wires having a distal end that is adapted to engage and push the vasoocclusive member through the catheter lumen as the pusher is advanced through the catheter. When the vasoocclusive member reaches the distal end of the catheter, it is discharged from the catheter by the pusher into the vascular site. This technique of discharging the vasoocclusive member from the distal end of the catheter has a number of undesirable limitations. First, because of the plunging action of the pusher and the vasoocclusive member, the positioning of the vasoocclusive member at the site cannot be controlled to a fine degree of accuracy. Second, once the vasoocclusive member has left the catheter, it is difficult to reposition or retrieve the vasoocclusive member if such is desired. Nevertheless, the technique has the benefit of delivering multiple vasoocclusive members at low cost with a short delivery time.

Several classes of techniques have been developed to enable more accurate placement of vasoocclusive members within a vessel. One class involves the use of electrolytic means to detach the vasoocclusive member from the pusher. In one technique (U.S. Pat. No. 5,122,136 to Guglielmi et al.) the vasoocclusive member is bonded via a metal-to-metal joint to the distal end of the pusher. The pusher and vasoocclusive member are made of dissimilar metals. The vasoocclusive member-carrying pusher is advanced through the catheter to the site and a low electrical current is passed through the pusher-vasoocclusive member assembly. The current causes the joint between the pusher and the vasoocclusive member to be severed via electrolysis. The pusher may then be retracted leaving the detached vasoocclusive member at an exact position within the vessel. In addition to enabling more accurate vasoocclusive member placement, the electric current may facilitate thrombus formation at the vasoocclusive member site. The only perceived disadvantage of this method is that the electrolytic release of the vasoocclusive member requires a period of time so that rapid detachment of the vasoocclusive member from the pusher does not occur. Other examples of this technique can be found in U.S. Pat. No. 5,423,829 to Pham et al. and U.S. Pat. No. 5,522,836 to Palermo.

Other forms of energy are also used to sever sacrificial joints that connect pusher and vasoocclusive member apparatus. An example is that shown in Japanese Laid-Open Patent Application No. 7-265431 or corresponding U.S. Pat. No. 5,759,161 to Ogawa et al. A sacrificial connection member, preferably made from polyvinylacetate (PVA), resins, or shape memory alloys, joins a conductive wire to a detention member. Upon heating by a monopolar high frequency current, the sacrificial connection member melts, severing the wire from the detention member.

In U.S. Pat. No. 4,735,201 to O'Reilly, an optical fiber is enclosed within a catheter and connected to a metallic tip on its distal end by a layer of hot-melt adhesive. The proximal end of the optical fiber is connected to a laser energy source. When endovascularly introduced into an aneurysm, laser energy is applied to the optical fiber, heating the metallic tip so as to cauterize the immediately surrounding tissue. The layer of hot-melt adhesive serving as the bonding material for the optical fiber and metallic tip is melted during this lasing, but the integrity of the interface is maintained by application of back pressure on the catheter by the physician. When it is apparent that the proper therapeutic effect has been accomplished, another pulse of laser energy is then applied to once again melt the hot-melt adhesive, but upon this reheating the optical fiber and catheter are withdrawn by the physician, leaving the metallic tip in the aneurysm as a permanent plug.

Another class of techniques for placing and detaching an embolic vasoocclusive member at a therapeutic site involves the use of mechanical attachment and release mechanisms, such as that shown in U.S. Pat. No. 5,261,916 to Engelson. In that technique, a vasoocclusive member having an enlarged portion is mated with a pusher having a keyway adapted to receive the enlarged portion of the vasoocclusive member in an interlocking relationship and covered by a coaxial member about the pusher and the vasoocclusive member. The coaxial member is movable by sliding the member axially. As the coaxial member is moved away from the junction where the vasoocclusive member's member engages the member of the keyway of the pusher, the vasoocclusive member disengages and the pusher is removed.

U.S. Pat. No. 5,304,195 to Twyford, Jr. et al. discloses a variation in which a vasoocclusive member and a pusher are each supplied with a ball on their proximal and distal ends, respectively. The portion of the vasoocclusive member and pusher containing the ball are radially biased and shaped to overlap each other so that when coupled, they maintain an interlocked position when enclosed within a coaxial sleeve. When the sleeve is retracted at the therapeutic site, the balls are allowed to move radially relative to one another to disengage and uncouple the pusher and vasoocclusive member.

In U.S. Pat. No. 5,350,397 to Palermo et al., a similar device is disclosed in which an embolic vasoocclusive member having an enlarged member, such as a ball, is released from a pusher assembly by forcing the enlarged member through an aperture in a socket situated on the distal end of a pusher assembly.

Another device for placement of vasoocclusive members is shown in U.S. Pat. No. 5,234,437 to Sepetka. This device includes a vasoocclusive member having a helical portion at one end and a pusher which is threaded to the inside of the helical vasoocclusive member by the use of a threaded section on the outside of the pusher. The device operates to release the vasoocclusive member by engaging the proximal end of the vasoocclusive member with a sleeve while the pusher is unthreaded. Once the pusher is free, the sleeve may be used to push the vasoocclusive member out into the treatment area.

U.S. Pat. No. 5,250,071 to Palermo discloses a vasoocclusive member and pusher assembly in which two interlocking clasps serve as a mechanical junction for the vasoocclusive member and pusher. The clasps may be supplied with apertures centrally aligned with the vasoocclusive member lumen for a control wire which, when axially withdrawn from the junction at the therapeutic site by the physician, leave the interlocking clasps free to separate, placing the vasoocclusive member at the desired therapeutic site. Alternatively, as shown in U.S. patent application Ser. No. 08/331,360, filed Dec. 21, 1994, similar self-disengaging interlocking clasps without such a control wire may be kept together by the catheter walls until released from the catheter; at that point, a simple twisting motion, gravity, fluid flow, or a combination thereof supplies the necessary force to uncouple the clasps.

The junction created by these mechanical attachment and release mechanisms is typically separable with some ease, i.e., usually by withdrawing a control wire, utilizing the built-in radial bias of the connecting members, torquing or unscrewing, or allowing gravity or fluid flow to facilitate separation in the case of self-disengaging clasps. It can still be difficult, however, to precisely control the exact moment at which that junction is separated, and premature separation due in part to a lack of adequate friction is always a possibility. In addition, those devices in which the junction is composed entirely of a either a sacrificial material, such as that taught by Japanese Laid-Open Patent Application No. 7-265431 or corresponding U.S. Pat. No. 5,759,161 to Ogawa et al, or an adhesive, such as the hot-melt adhesive disclosed in U.S. Pat. No. 4,735,201 to O'Reilly, may be prone to reliability problems as the security of a mechanically interlocking or attachable clasp or other mechanism is absent.

Accordingly, none of these disclosed devices teaches or suggests a vasoocclusive member assembly having a friction-enhancing mechanical detachment junction by the addition of a thermoplastic member that does not soften until radio frequency energy is administered to the assembly. This combination allows for improved reliability and a higher degree of control over the release of the vasoocclusive member into the therapeutic site without sacrificing the integrity intrinsic to a mechanical detachment junction.

SUMMARY OF THE INVENTION

This invention is a device for placing detachable vasoocclusive devices within the vasculature of the human body so to occlude that site with the vasoocclusive member. This device includes a vasoocclusive member with opposing ends having, on at least one end, a detachable vasoocclusive member junction attachable to a pusher junction, a pusher comprising an elongated member having a proximal end and a distal end, the distal end formed by a pusher junction attachable to the detachable vasoocclusive member junction, and a thermoplastic member adhering to both the vasoocclusive member junction and the pusher junction to aid in preventing disengagement of both the detachable vasoocclusive member junction and the pusher junction until the application of radio frequency energy in an amount sufficient to soften the thermoplastic member. A coil, which can be helical, and which can have a random or straight configuration, is an example of such a vasoocclusive member that is within the scope of this invention. Additionally, the thermoplastic member can encapsulate the vasoocclusive member junction and the pusher junction, and the proximal end of the pusher can be electrically insulated as well.

Another aspect of the invention is a combination conducting core wire-vasoocclusive member assembly for use in occluding a selected vascular site within a vessel. The vasoocclusive member has opposing ends with an axially central lumen therethrough, a conducting core wire with a distal end adaptable for receiving radio frequency energy, and a thermoplastic member adhering to both the vasoocclusive member and the conducting core wire to aid in preventing disengagement of the vasoocclusive member and the conducting core wire until the application of radio frequency energy in an amount sufficient to soften the thermoplastic member. A coil, which can be helical, and which can have a random or straight configuration, is an example of such a vasoocclusive member that is within the scope of this invention. Additionally, the thermoplastic member can encapsulate the vasoocclusive member and the conducting core wire, and the proximal end of the conducting core wire can be electrically insulated as well.

A further aspect of the invention is a process for the placement of a vasoocclusive member at a selected site comprising the steps of: (a) introducing to a selected site a vasoocclusive member having, on at least one end, a detachable vasoocclusive member junction engaged with a pusher junction, a thermoplastic member adhering to both the detachable vasoocclusive member junction and the pusher junction to aid in preventing their disengagement; (b) applying radio frequency energy to both the detachable vasoocclusive member junction and the pusher junction in an amount sufficient to substantially soften the thermoplastic member and aid the release of the vasoocclusive member into the selected site; and (c) moving the pusher junction out of engagement with the vasoocclusive member. A coil, which can be helical, and which can have a random or straight configuration, is an example of such a vasoocclusive member that is within the scope of this invention.

Still another aspect of this invention is a process for the placement of a vasoocclusive member at a selected site comprising the steps of: (a) attaching a thermoplastic member to the distal end of a conducting core wire; (b) joining the distal end of the conducting core wire to a vasoocclusive member to form a combination conducting core wire-vasoocclusive member assembly; (c) introducing to a selected site the combination conducting core wire-vasoocclusive member assembly; (d) applying radio frequency energy to the combination conducting core wire-vasoocclusive member assembly in an amount sufficient to substantially soften the thermoplastic member and aid the release of the vasoocclusive member into the selected site; and (e) moving the conducting core wire out of engagement with the vasoocclusive member. A coil, which can be helical, and which can have a random or straight configuration, is an example of such a vasoocclusive member. The conducting core wire may be attached to the vasoocclusive member prior to attaching the thermoplastic member to the conducting core wire.

DESCRIPTION OF THE INVENTION

Figure 1A:
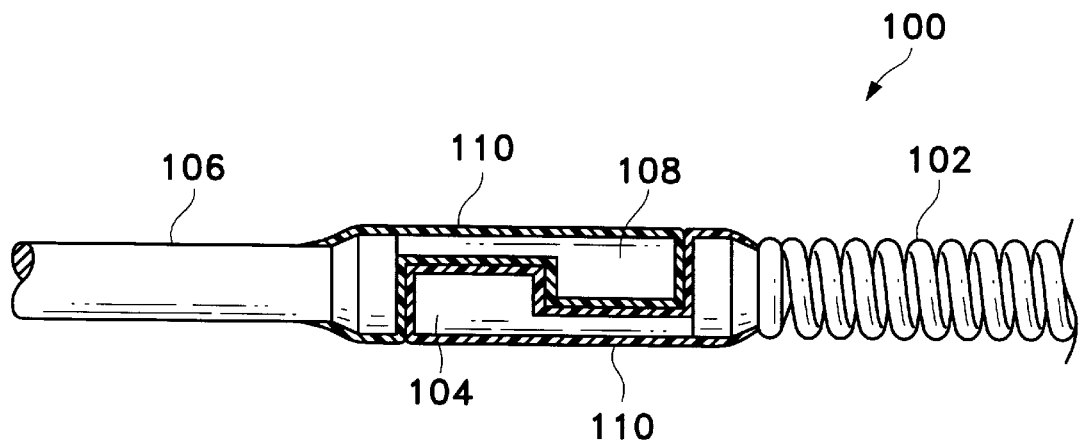
FIGS. 1A and 1B are partial sectional views of two examples of the combination pusher-vasoocclusive member assembly of the present invention with a thermoplastic member adhering to the assembly.
Figure 1B:
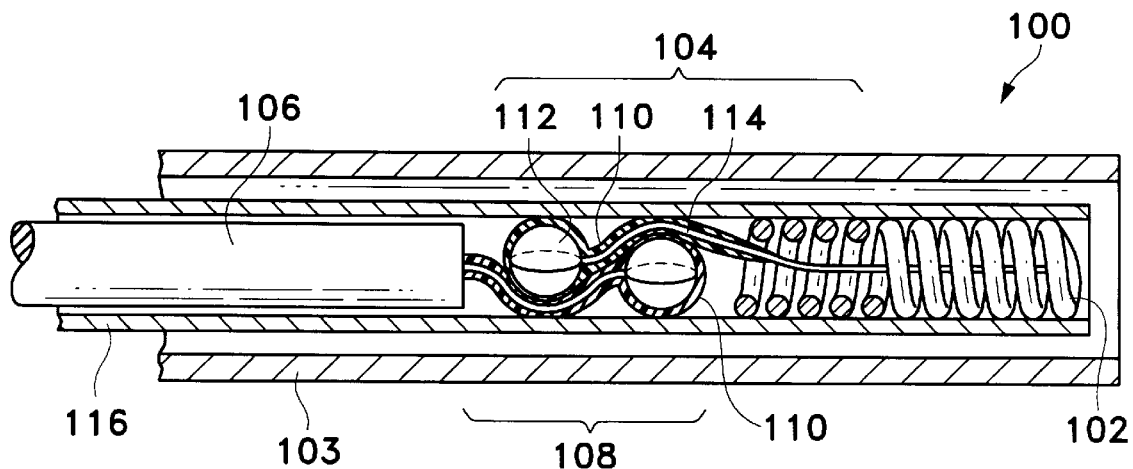

Two variations of the combination pusher-vasoocclusive member assembly (100) are shown in FIGS. 1A and 1B. In both figures, the vasoocclusive member (102) is shown as a coil that is helical in form, although it may be any other suitable vasoocclusive device or form, such as a ribbon, a braided member, or the like. The vasoocclusive member (102) should be of a size sufficiently small that it may be advanced through a catheter (103), shown only in FIG. 1B, that is appropriately sized for accessing the targeted vascular site. For instance, when accessing a brain aneurysm in a small vessel, an appropriately sized catheter is quite small and very flexible. The vasoocclusive member in such a situation must be small enough to fit through the catheter and out its distal end at the treatment site.

The vasoocclusive member (102) is desirably made up of a radiopaque, physiologically compatible material. For instance, the material may be platinum, gold, tungsten, or alloys of these. Certain polymers are also suitable as vasoocclusive member material either alone or in conjunction with metallic markers providing radiopacity. These materials are chosen so that the procedure of locating the vasoocclusive member within the vessel may be viewed using radiography. However, it is also contemplated that the vasoocclusive member may be made of various other biologically inert polymers or of carbon fiber.

When the vasoocclusive member is a coil, its shape and constituent winding will depend upon the use to which the coil will be placed. For occluding peripheral or neural sites, the coils will typically be made of 0.05 to 0.15 mm diameter wire (platinum or platinum/tungsten alloy) that may be wound to have an inner diameter of 0.15 to 1.5 mm with a minimum pitch—that is to say that the pitch is equal to the diameter of the wire used in the coil. The outer diameter is then typically between 0.25 mm to 1.8 mm. The length of the coil will normally be in the range of 0.5 to 60 cm, preferably 0.5 to 40 cm.

If desired, the coil may be formed in such a way that the coil is essentially linear as it passes through the catheter and yet assumes a randomly oriented relaxed condition after it is released from the distal end of the catheter. A discussion of this variation may be found in U.S. Pat. No. 4,994,069 to Ritchart et al.

Turning now to the embodiment of FIG. 1A, fixedly attached to vasoocclusive member (102) is vasoocclusive member junction (104). Likewise, fixedly attached to pusher (106) is pusher junction (108). Prior to using the assembly of FIG. 1A in a selected site, vasoocclusive member junction (104) and pusher junction (108) are mechanically interlocked, or engaged, to each other. For purposes of this invention, the term "engaged" is herein used to describe any mechanical or physical attachment, interlocking, mating, binding, coupling, hooking, etc., such that members that are said to be "engaged" do not come apart or detach from one another without some positive effort or motion specifically in the absence of the thermoplastic member (110) discussed below.

The particular mechanical engagement configuration shown in FIG. 1A created between the vasoocclusive member junction (104) and the pusher junction (108) is discussed more thoroughly in U.S. Pat. No. 5,250,071 to Palermo and U.S. patent application Ser. No. 08/331,360.

FIG. 1B depicts an embodiment of the present invention in the mechanical engagement configuration disclosed by Twyford, Jr. et al in U.S. Pat. No. 5,304,195. In this device, the vasoocclusive member (102) and pusher (106) are again supplied with vasoocclusive member junction (104) and pusher junction (108), respectively. However, in this embodiment, both vasoocclusive member junction (104) and pusher junction (108) are each comprised of a ball (112) disposed at the end of a wire (114). As previously discussed, the portion of the vasoocclusive member junction (104) and pusher junction (108) containing the ball (112) and wire (114) are radially biased and shaped to overlap each other so that when coupled, they maintain an interlocked position when enclosed within a coaxial sleeve (116).

Each of the mechanical engagement configurations depicted in FIGS. 1A and 1B are but two of many ways in which a vasoocclusive member can be mechanically engaged to a pusher or other similar device. These configurations are presented for purposes of illustration only and do not limit the scope of the types of mechanical engagement configurations that may be used with the present invention. As will be clear to those skilled in the art, a wide variety of mechanical engagement configurations can be used to effectively practice this invention. These additionally include, for example, those configurations found in U.S. Pat. No. 5,261,916 to Engelson, U.S. Pat. No. 5,350,397 to Palermo et al., U.S. Pat. No. 5,234,437 to Sepetka, and U.S. Pat. No. 5,578,074 to Mirigian.

Attention is now directed to a preferred configuration of the thermoplastic member (110) as it adheres to the pusher-vasoocclusive member assembly (100) shown in FIGS. 1A and 1B. The enhanced thickness of the thermoplastic member (110) as shown in FIGS. 1A and 1B is not necessarily to scale and is depicted as such for purposes of illustration only.

In this configuration, a thermoplastic material is deposited by any conventional technique to coat substantially the entire surface area of vasoocclusive member junction (104) and pusher junction (108) of FIGS. 1A and 1B. One technique, for example, is dipping or coating these members in molten or substantially softened thermoplastic material, but other techniques as known in the art, such as shrink-wrapping, spraying on in the form of a suspension or latex, or others may be used as well. As will be described in greater detail, one object of coating substantially the entire surface area of these members is to electrically insulate assembly (100) to limit the heating effect of the energy applied during deployment of vasoocclusive member (102).

Next, prior to the passing of time to allow substantial hardening of the thermoplastic material, the junctions are physically engaged to form the assembly (100) as shown in FIGS. 1A and 1B prior to insertion of the assembly inside a catheter (103) (shown only in FIG. 1B). In the case of the embodiment of FIG. 1B, assembly (100) is first placed inside sleeve (116) before it is placed inside catheter (103).

The integrity of the newly-formed joint is primarily maintained by the locking effect of the mechanical engagement mechanisms as previously described. However, the fit of this joint need not be close, as these various mechanisms are augmented by the adhesive and friction-enhancing effects obtained when the thermoplastic coating on each member solidifies after mechanical engagement to form thermoplastic member (110).

A preferred thermoplastic material for thermoplastic member (110) is polyvinylacetate (PVA), although any suitable, biologically inert thermoplastic polymer with the proper transition temperature (herein defined as any safe temperature above that of the fluids of the human body which allows for the safe, efficient, and reliable detachment of the vasoocclusive member (102) into the selected site) may be used. Examples of such other thermoplastics that may be used singly or in combination include, but are not limited to, materials such as polyactide, polyglycolide, polyactide-co-glycolide polydioxanone, polyethylene, polyiminocarbonates, polycaprolactone, polyesters and the like. U.S. Pat. No. 5,292,321 to Lee discusses such thermoplastic materials.

The thermoplastic member (110) may take on a variety of thicknesses and coverage configurations depending upon a number of factors such as the type of mechanical engagement configuration used, the degree of control over the release of the vasoocclusive member (102) into the selected site desired by the user, the types and combinations of materials used, dimensional constraints of the catheter and sheath, and so forth. For example, prior to insertion of the assembly (100) inside catheter (103), thermoplastic member (110) may be further augmented by encapsulating the engaged members in additional thermoplastic material, such as by dipping the entire engaged joint of assembly (100) in molten or substantially softened thermoplastic material, although this is not necessary. Among others benefits, this would further enhance the integrity of the joint of assembly (100).

For all configurations, it is desired that the thermoplastic member (110) have a thickness that will not prohibit the engaged junctions from freely moving within a catheter sheath or other associated equipment necessary to accomplish the desired objective of reliably and safely placing a vasoocclusive member at a selected site.

Figure 2A:
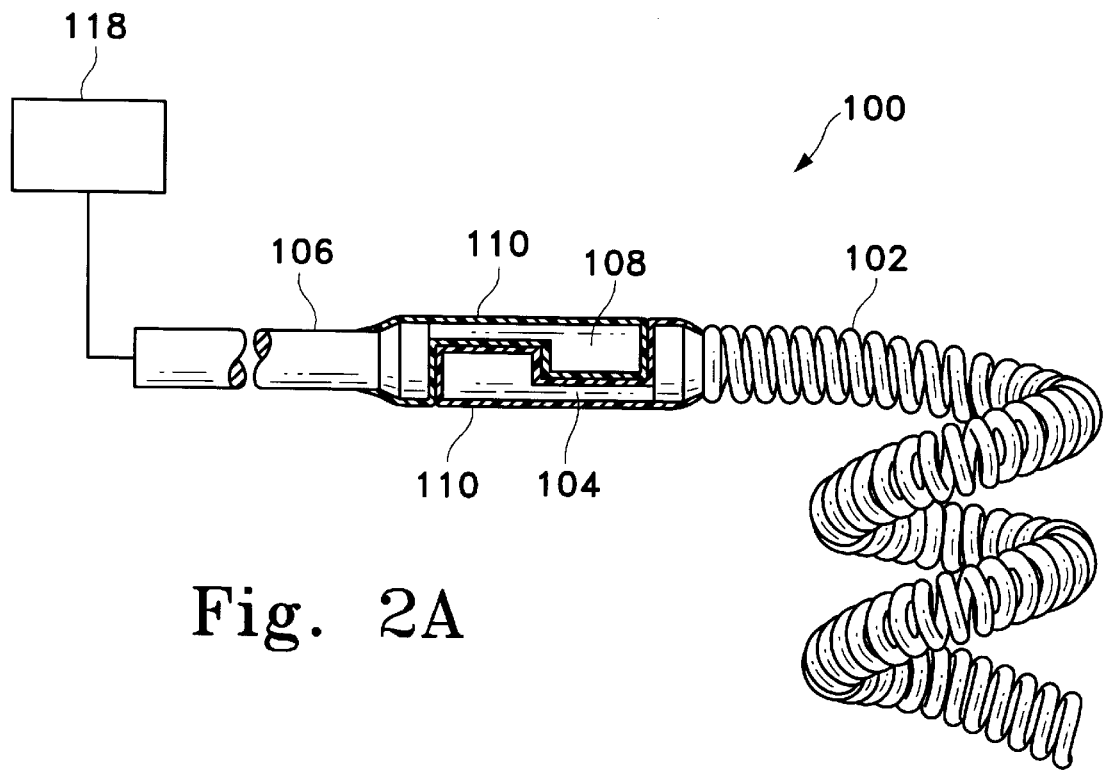
FIGS. 2A and 2B show, in partial sectional view, the operation of a variation of the combination pusher-vasoocclusive member assembly of the present invention as it places a vasoocclusive member within a target site.
Figure 2B:
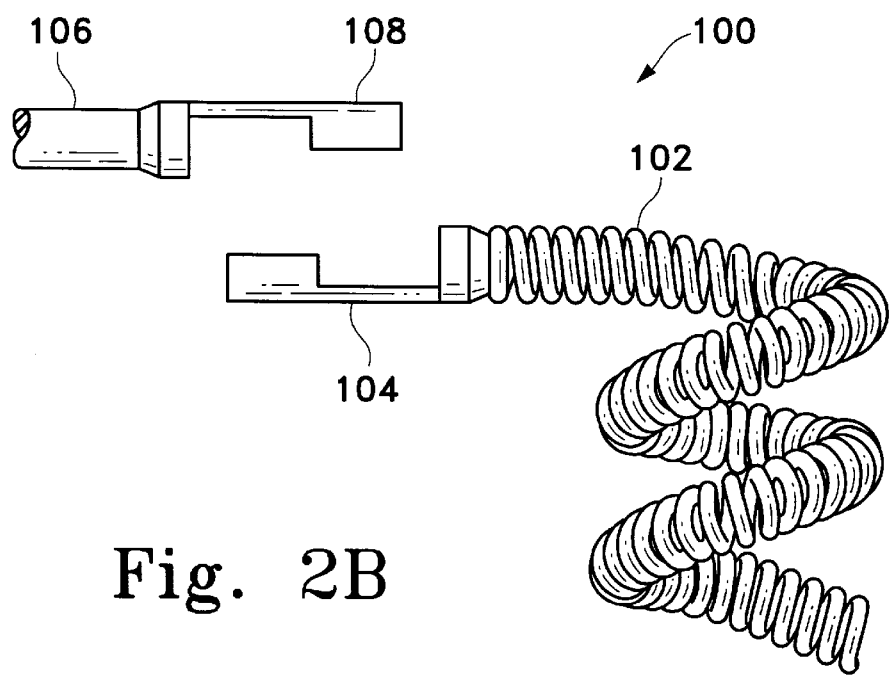

FIGS. 2A and 2B show, in partial cross-section, the combination pusher-vasoocclusive member assembly (100) of FIG. 1A in operation. In FIG. 2A, an energy source (118) is connected to the combination pusher-vasoocclusive member assembly (100). In this embodiment, vasoocclusive member (102) is typically a coil as shown in FIGS. 2A and 2B. The coil is shown as helical in form, although it may be any other suitable form.

Conventional catheter insertion and navigational techniques involving guidewires or flow-directed devices may be used to access the site with a catheter (not shown). Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the pusher (106) having the vasoocclusive member (102) at the distal end is advanced through the catheter. The pusher (106) is advanced past the distal end of the catheter so that the vasoocclusive member (102) is free of the catheter and with the vasoocclusive member (102) positioned precisely at the desired treatment site.

The length of pusher (106) will be such as to be capable of being advanced entirely through the catheter to place vasoocclusive member (102) at the target site but yet with a sufficient portion of the distal end of the pusher (106) protruding from the distal end of the catheter to enable detachment of the vasoocclusive member (102). For use in peripheral or neural surgeries, the pusher will normally about 100–200 cm in length, more normally 130–180 cm in length. The diameter of the pusher is usually in the range of 0.25 to about 0.90 mm.

Once the vasoocclusive member (102) is at the selected site, energy, preferably radio frequency energy, is then supplied by the energy source (118) and transmitted through pusher (106) to pusher junction (108) and vasoocclusive member junction (104) so to heat the thermoplastic member (110) above its transition temperature until it is sufficiently softened or dissipated to free vasoocclusive member junction (104) and vasoocclusive member (102) as shown in FIG. 2B. The entire catheter may then be removed or the pusher (106) may be withdrawn from the catheter lumen to provide for installation of other vasoocclusive members. If additional vasoocclusive members are to be placed at the target site, the procedure is repeated. After the desired number of vasoocclusive members have been placed at the site, the catheter is withdrawn from the vessel.

As previously described, prior to the formation of assembly (100), it is desired to ensure that the thermoplastic material forming thermoplastic member (110) coats substantially the entire surface of each of the vasoocclusive member junction (104) and pusher junction (108) to electrically insulate the combination pusher-vasoocclusive member assembly (100). Electrical insulation helps to limit the heating effect of the energy, applied to soften the thermoplastic member (110), to the joined vasoocclusive member junction (104) and pusher junction (108) in the immediate vicinity of the thermoplastic member (110) and to avoid excessive undesirable heating of the pusher (106) and the vasoocclusive member (102). This concept is described in a different context in U.S. patent application Ser. No. 08/607,592, filed Feb. 27, 1996.

Figure 3:
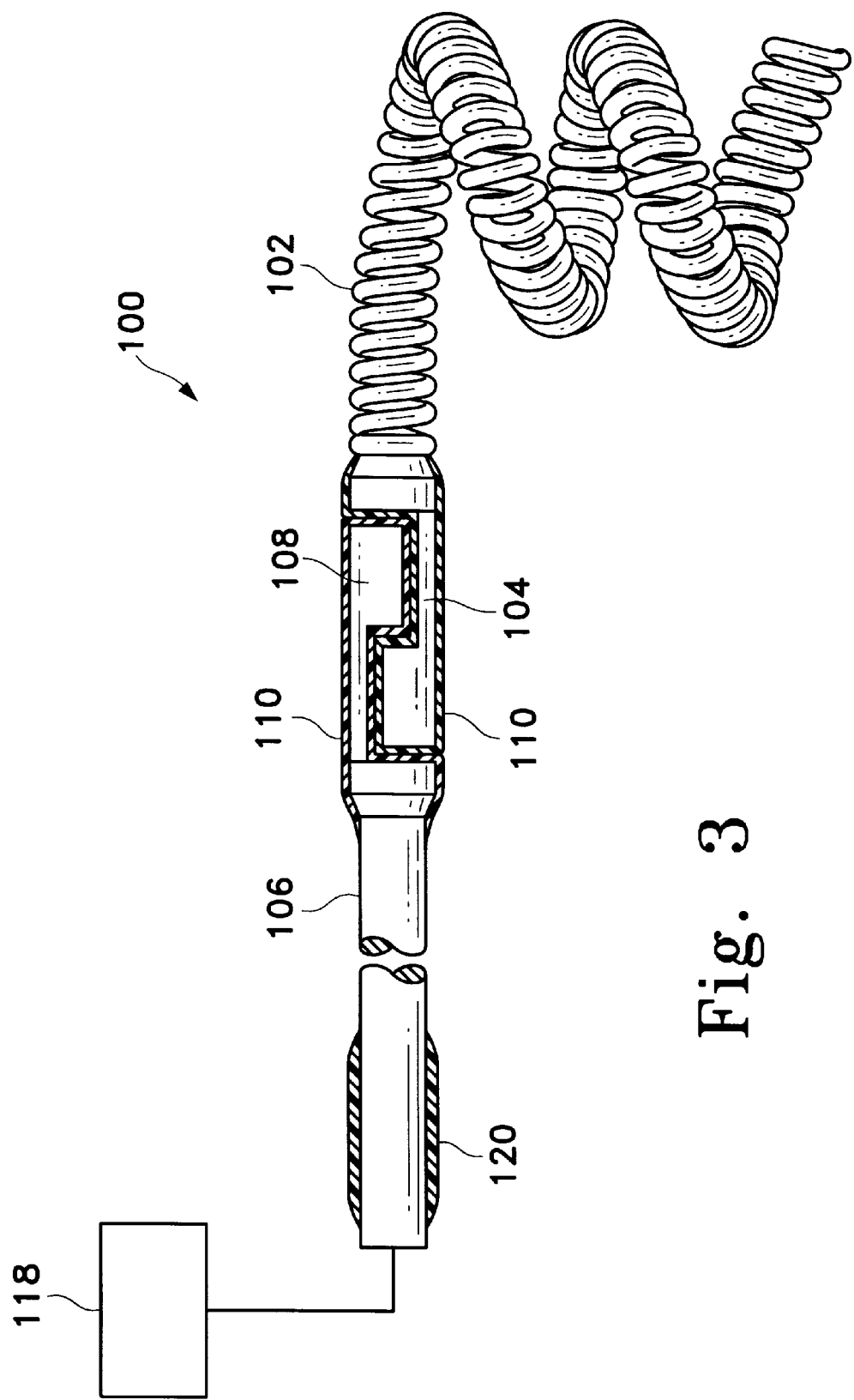
FIG. 3 is a partial sectional view of a variation of the combination pusher-vasoocclusive member assembly of the present invention additionally consisting of electrical insulation on the proximal end of the pusher.

Alternatively, as depicted in FIG. 3, if it is desired to further protect the assembly (100) from heating effects during detachment, an additional electrical insulating member (120) may be affixed to the proximal section of pusher (106). If such an additional insulating member (120) is used, it is desired, but not necessary, that it consist of an electrically insulating polymer material and/or thickness different from that of the thermoplastic member (110) such that the thermoplastic member (110) preferentially absorbs the energy applied during detachment by the energy source (118). The insulating material can be a polymer such as polyethylene, polypropylene, polyurethane, polyethylene terephthalate, polyvinylchloride, and is preferably a polymer from the class of polymers generally known as parylene. The insulation may be applied to the proximal end of pusher (106) by a number of processes such as shrink-wrapping, dipping in molten polymer, spraying on in the form of a suspension or latex, or the like. The axial length of the additional insulating member (120) and its thickness may vary depending upon the degree of additional electrical insulation desired, the specific configuration of the assembly (100), the application for which assembly (100) is used, etc.

Figure 4A:
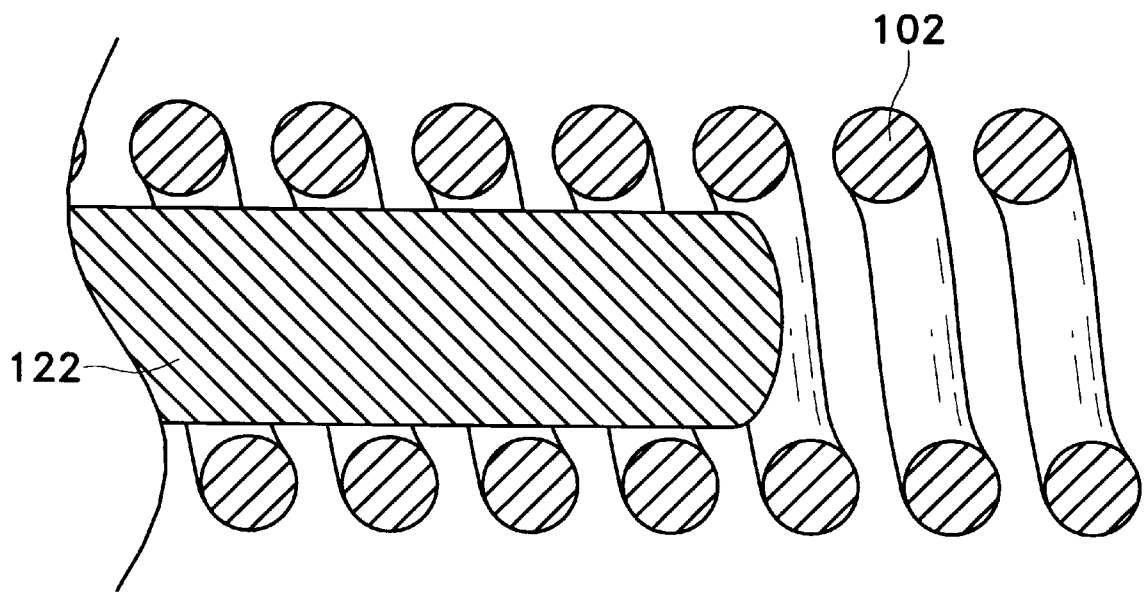
FIG. 4A is a partial sectional view of a variation of the combination conducting core wire-vasoocclusive member assembly of the present invention prior to the application of a thermoplastic member to the assembly.
Figure 4B:
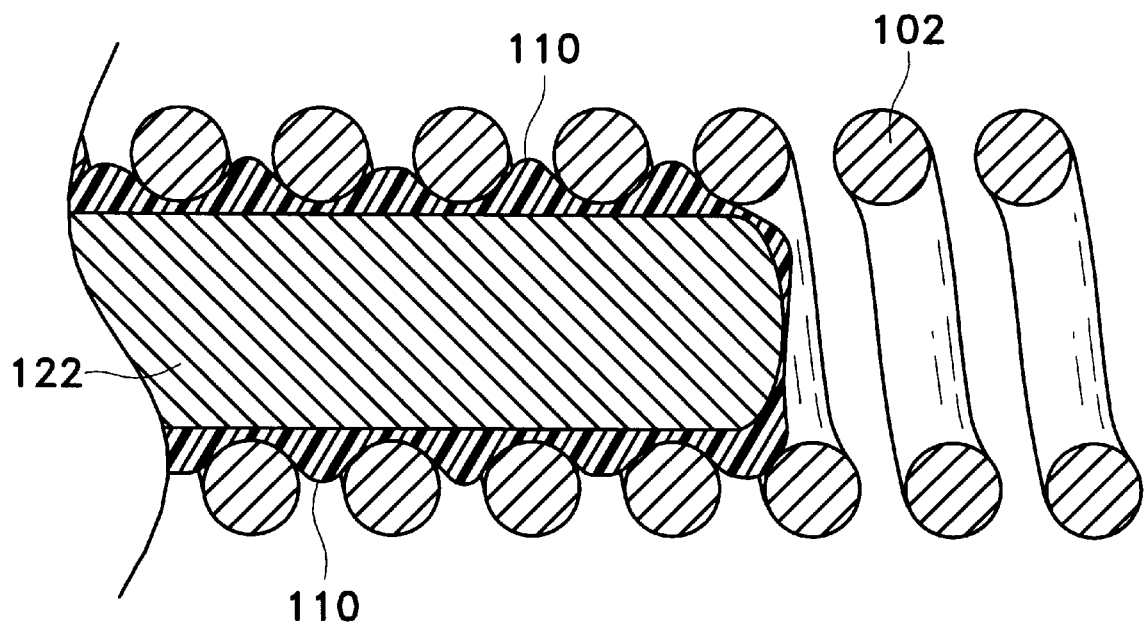
FIG. 4B is a partial sectional view of an example of the combination conducting core wire-vasoocclusive member assembly of the present invention with a thermoplastic member adhering to the assembly.

FIGS. 4A and 4B are partial cross-sectional views that show a variation of the present invention in which a vasoocclusive member (102) is engaged by a friction fit with the distal end of conducting core wire (122). Again, the vasoocclusive member (102) is shown in this embodiment as a coil. This variation can be assembled using a variety of techniques. The technique depicted in FIGS. 4A and 4B is as follows: a conducting core wire (122), whose diameter is chosen to enable a friction fit between it and the inner diameter of vasoocclusive member (102), is connected to an energy source (not shown) at its proximal end. Either prior to or after insertion into the vasoocclusive member (102) proximal end, a thermoplastic member (110) is attached to the distal end of conducting core wire (122). It is preferable that this connection take place after insertion of the distal end of conducting core wire (122) into the vasoocclusive member (102). The thermoplastic member (110) may be attached by any conventional means, such as line of sight spray deposition, the result of which is depicted in FIG. 4B. As can be seen in FIG. 4B, thermoplastic member (110) has been deposited on conducting core wire (122) after the insertion of the distal end of conducting core wire (122) into the vasoocclusive member (102). The line of sight process deposits thermoplastic material between coil windings around the entire circumference of the vasoocclusive member (102) such that an excess of thermoplastic material builds up on the conducting core wire (122) regions aligned with the gaps between coil windings. As the deposition process continues, thermoplastic material begins to impinge upon the surfaces of the coil windings on the coil's inner diameter. Once a sufficient thickness of the thermoplastic member (110) has been obtained, a friction fit between the distal end of conducting core wire (122) and the vasoocclusive member (102) exists. This friction fit aids in maintaining the integrity of the mechanical joint created by the insertion of the distal end of conducting core wire (122) into the vasoocclusive member (102).

As previously indicated, the thermoplastic member (110) may also be deposited on the distal end of conducting core wire (122) prior to its insertion into the vasoocclusive member (102). This may be preferred, for instance, for ease of manufacture and to allow greater flexibility in the choice of thermoplastic member material, deposition process, assembly process, etc. In any event, it is desired that the distal end of conducting core wire (122) be electrically insulated from vasoocclusive member (102) by thermoplastic member (110) as previously described.

Operation of the embodiment of FIGS. 4A and 4B is similar to that of the operation described for the embodiment of FIGS. 2A and 2B. Once the vasoocclusive member (102) is at the selected site, energy, preferably radio frequency energy, is supplied by the energy source (118) and transmitted through conducting core wire (122) so to heat the thermoplastic member (110) above its transition temperature until it is sufficiently softened. At this point, vasoocclusive member (102) is free. The entire catheter may then be removed or the conducting core wire (122) may be withdrawn from the catheter lumen to provide for installation of other vasoocclusive members. If additional vasoocclusive members are to be placed at the target site, the procedure is repeated. After the desired number of vasoocclusive members have been placed at the site, the catheter is withdrawn from the vessel.

Modifications of the device described above and methods of using it in keeping with this invention that are apparent to those having skill in this mechanical and surgical instrument design art and related fields are intended to be within the scope of the claims which follow.

What is claimed is:

1. A combination pusher-vasoocclusive member assembly for use in occluding a selected vascular site within a vessel comprising:

(a) a vasoocclusive member with opposing ends having, on at least one end, a detachable vasoocclusive member junction engageable to a pusher junction;

(b) a pusher comprising an elongated member having a proximal end and a distal end, the distal end forming a pusher junction engageable to the detachable vasoocclusive member junction;

(c) a source of radio frequency energy attachable to the pusher; and (d) a thermoplastic member adhering to both the vasoocclusive member junction and the pusher junction to aid in preventing disengagement of both the detachable vasoocclusive member junction and the pusher junction until the application of radio frequency energy in an amount sufficient to soften the thermoplastic member and to allow disengagement to take place.

2. The combination of claim 1 wherein the thermoplastic member additionally encapsulates the vasoocclusive member junction and the pusher junction.

3. The combination of claim 1 wherein the proximal end of the pusher is electrically insulated.

4. The combination of claim 1 where the vasoocclusive member is a coil.

5. The combination of claim 4 where the coil is helical.

6. The combination of claim 4 where the coil has a random or straight configuration.

7. A combination conducting core wire-vasoocclusive member assembly for use in occluding a selected vascular site within a vessel comprising:

(a) a vasoocclusive member with opposing ends having an axially central lumen therethrough;

(b) a conducting core wire having a proximal end and a distal end for receiving radio frequency energy;

(c) a source of radio frequency energy attachable to the pusher; and (d) a thermoplastic member adhering to both the vasoocclusive member and the conducting core wire to aid in preventing disengagement of both the vasoocclusive member and the conducting core wire until the application of radio frequency energy in an amount sufficient to soften the thermoplastic member.

8. The combination of claim 7 where the thermoplastic member additionally encapsulates the vasoocclusive member and the conducting core wire.

9. The combination of claim 7 where the proximal end of the conducting core wire is electrically insulated.

10. The combination of claim 7 where the vasoocclusive member is a coil.

11. The combination of claim 10 where the coil is helical.

12. The combination of claim 10 where the coil has a random or straight configuration.

13. A process for the placement of a vasoocclusive member at a selected site comprising the steps of:

(a) introducing to a selected site, a vasoocclusive member having, on at least one end, a detachable vasoocclusive member junction engaged with a pusher junction, a thermoplastic member adhering to both the detachable vasoocclusive member junction and the pusher junction to aid in preventing their disengagement;

(b) applying radio frequency energy to both the detachable vasoocclusive member junction and the pusher junction in an amount sufficient to substantially soften the thermoplastic member and aid the release of the vasoocclusive member into the selected site; and (c) moving the pusher junction out of engagement with the vasoocclusive member.

14. The process of claim 13 where the vasoocclusive member is a coil.

15. The process of claim 14 where the coil is helical.

16. The process of claim 14 where the coil has a random or straight configuration.

17. A process for the placement of a vasoocclusive member at a selected site comprising the steps of:

(a) attaching a thermoplastic member to the distal end of a conducting core wire;

(b) joining the distal end of the conducting core wire to a vasoocclusive member to form a combination conducting core wire-vasoocclusive member assembly;

(c) introducing to a selected site the combination conducting core wire-vasoocclusive member assembly;

(d) applying radio frequency energy to the combination conducting core wire-vasoocclusive member assembly in an amount sufficient to substantially soften the thermoplastic member and aid the release of the vasoocclusive member into the selected site; and (e) moving the conducting core wire out of engagement with the vasoocclusive member.

18. The process of claim 17 where the conducting core wire is attached to the vasoocclusive member prior to attaching the thermoplastic member to the conducting core wire.

19. The process of claim 17 where the vasoocclusive member is a coil.

20. The process of claim 19 where the coil is helical.

21. The process of claim 19 where the coil has a random or straight configuration.

* * * * *